(12) United States Patent
Benassi et al.

(10) Patent No.: US 10,046,176 B2
(45) Date of Patent: Aug. 14, 2018

(54) RADIOTHERAPY SYSTEM PROVIDED WITH A PROGRAM FOR THE CALCULATION OF THE INTENSITY OF AN ELECTRONS BEAM

(71) Applicant: ISTITUTI FISIOTERAPICI OSPITALIERI, Rome (IT)

(72) Inventors: Marcello Benassi, Rome (IT); Lidia Strigari, Rome (IT); Sandro Carpino, Rome (IT); Marco D'Andrea, Rome (IT); Antonella Soriani, Rome (IT); Giuseppe Iaccarino, Rome (IT)

(73) Assignee: ISTITUTI FISIOTERAPICI OSPITALIERI, Rome (IT)

( * ) Notice: Subject to any disclaimer, the term of this patent is extended or adjusted under 35 U.S.C. 154(b) by 114 days.

(21) Appl. No.: 14/894,472

(22) PCT Filed: May 28, 2014

(86) PCT No.: PCT/IT2014/000147
§ 371 (c)(1),
(2) Date: Nov. 27, 2015

(87) PCT Pub. No.: WO2014/192034
PCT Pub. Date: Dec. 4, 2014

(65) Prior Publication Data
US 2016/0121137 A1    May 5, 2016

(30) Foreign Application Priority Data
May 30, 2013 (IT) .............................. RM2013A0314

(51) Int. Cl.
*A61N 5/10*    (2006.01)

(52) U.S. Cl.
CPC .......... *A61N 5/1031* (2013.01); *A61N 5/1039* (2013.01); *A61N 5/1065* (2013.01);
(Continued)

(58) Field of Classification Search
CPC .......... A61N 5/1031; A61N 2005/1034; A61N 5/1065; A61N 5/1077; A61N 2005/1089; A61N 5/1039; A61N 5/1071
See application file for complete search history.

(56) References Cited

U.S. PATENT DOCUMENTS

2005/0101824 A1* 5/2005 Stubbs ................. A61N 5/1015
600/3
2007/0195929 A1* 8/2007 Ruchala ............... A61N 5/1048
378/65

(Continued)

FOREIGN PATENT DOCUMENTS

| EP | 1 977 78 A2 | 10/2008 |
|---|---|---|
| EP | 2 269 693 A1 | 5/2011 |
| WO | 2012/032477 A1 | 3/2012 |

OTHER PUBLICATIONS

1-International Search Report issued for International Application No. PCT/IT2014/000147 filed on May 28, 2014 in the name of Istituto Fisioterapici Ospitalieri. dated Sep. 29, 2014.
(Continued)

*Primary Examiner* — Christine H Matthews
*Assistant Examiner* — Joshua D Lannu
(74) *Attorney, Agent, or Firm* — Steinfl + Bruno, LLP

(57) ABSTRACT

A system for radiotherapy includes an accelerator of an electron beam, an imaging apparatus, a control unit and a radiation dose sensor connected to the control unit equipped with a program configured to execute the steps: setting a first intensity of the electron beam, according to a predefined image of a target zone, the intensity to be emitted in a first radiation; operating said accelerator to emit the first radiation being a fraction of the first intensity; detecting a real intensity during the first radiation by the radiation dose sensor; acquiring an image of the zone; calculating an intermediate intensity according to the image acquired in the
(Continued)

step and according to the real intensity; and comparing the first intensity with the intermediate intensity to calculate a final beam intensity for a subsequent second radiation.

7 Claims, 4 Drawing Sheets

(52) U.S. Cl.
CPC ......... *A61N 5/1071* (2013.01); *A61N 5/1077* (2013.01); *A61N 2005/1034* (2013.01); *A61N 2005/1089* (2013.01)

(56) References Cited

U.S. PATENT DOCUMENTS

2009/0018403 A1* 1/2009 Black .................. A61B 5/0031
600/300

2012/0140887 A1* 6/2012 Mundy ................ A61N 5/1048
378/65

OTHER PUBLICATIONS

2-Written Opinion issued for International Application No. PCT/IT2014/000147 filed on May 28, 2014 in the name of Istituto Fisioterapici Ospitalieri. dated Sep. 29, 2014.

3-International Preliminary Report on Patentability issued for International Application No. PCT/IT2014/000147 filed on May 28, 2014 in the name of Istituto Fisioterapici Ospitalieri. dated May 4, 2015.

4-Search Report issued for Italian Patent Application No. RM201300314 filed on May 30, 2013 in the name of Istituto Fisioterapici Ospitalieri Completion date: Nov. 12, 2013.

4-Written Opinion issued for Italian Patent Application No. RM201300314 filed on May 30, 2013 in the name of Istituto Fisioterapici Ospitalieri Completion date: Nov. 12, 2013.

* cited by examiner

RADIOTHERAPY SYSTEM PROVIDED WITH A PROGRAM FOR THE CALCULATION OF THE INTENSITY OF AN ELECTRONS BEAM

CROSS REFERENCE TO RELATED APPLICATIONS

The present application is the U.S. national stage entry of International Patent Application No. PCT/IT2014/000147, filed internationally on May 28, 2014, which, in turn, claims priority to Italian Patent Application No. RM2013A000314, filed on May 30, 2013.

The present invention relates to a radiotherapy system provided with a program for the calculation of the intensity of an electrons beam.

More specifically, the invention concerns a system or apparatus of the above kind, studied and realized in particular to simulate the intensity calculation of an electrons beam that can be administered in intra-operative radiotherapy to be achieved during the removal of the tumor mass but which can be used for any intra-operative radiotherapy treatment, of which the intensity calculation of the electron beam to be administered is necessary.

As it is well known, currently, following a conservative surgical intervention, i.e., after the removal of a part of the body, in which a tumor mass is present, it is resorted to the conventional external beam radiotherapy that conveys high energy X-rays through the skin, to release the X-rays dose within the predetermined zone to be irradiated, in order to sterilize the remaining part, in particular the tumor bed, which is the zone of the body where the tumor lesion was present prior to surgical resection, so as to reduce the risk of local relapses.

Generally, in conventional radiotherapy, the total dose required is given in several fractions, resulting in the need for the patient to access dozens of times at the health care facility.

It seems evident that this procedure is burdensome both for the considerable discomfort to patients, and for the strong economic and organizational impact to which the radiotherapy departments are involved to.

Additionally, by this type of treatments, generally delivered through photons, it is not possible to completely avoid the irradiation of healthy tissues and organs close to the tumor areas, which can compromise the normal function of these organs and tissues.

Therefore intra-operative radiotherapy (IORT) as a technical replacement and/or supplemental of the conventional radiotherapy is recently developed.

IORT mainly consists in the administration, during the surgical removal of the tumor mass, of a single high dose of radiation, delivered directly to the tumor bed, with the purpose of sterilizing the tumor cells remaining after surgical resection.

The main benefits of the IORT reside in the fact that, using electron beams of appropriate energy, it is possible to provide directly on the target volume, during surgery in a single treatment session, a treatment dose saving at the same time healthy tissue that can be completely shielded or temporarily removed from the treated zone during irradiation.

In particular, IORT is already routinely used for treating some superficial tumors (breast, head, neck) and deep tumors (prostate, rectum) and bring significant benefits to the Regional or National Health Service as it significantly reduces the waiting lists of patients for the access to the radiotherapy departments, as the treatment is performed in a single session, at the same surgery.

Clinical experience suggests that the biological effectiveness of single-dose administration is larger than the effect that the same dose would have been fractionated. According to radiobiological estimates (Strandquist 1994, Okunieff 1999) a single IORT dose could produce a tumoricidal effect about 2 or 3 times greater than the same dose administered in a full course of fractionated external beam radiation therapy.

Indeed, the clear time reduction between tumor surgical excision and the tumor irradiation decreases significantly the regrowth risk of the tumor mass due to residual tumor cells, with clinical and logistical undoubted advantages for the patient.

This method is essential in cases in which the action of surgical removal of the tumor mass is not fully effective or it is difficult due to the presence of structures or critical organs, which may be damaged or cut during surgery, or if a high risk of microscopic infiltration of the tumor bed is present.

In addition, it is possible to prevent that the radiation beam affects healthy organs, which can be appropriately shielded and protected during surgery.

Currently, the value of the dose delivered to the tumor bed is checked by measurements with in vivo dosimetry, by placing a detector dose in a significant reference point within the radiation field, or in the opening of the tumor bed.

A prior art example closest to the invention at issue is represented by the European patent application EP 2269693, which relates to a simulation and planning system for IORT and the corresponding method.

This system includes a central processing unit for the management of the system and the interface with the user, a plurality of monitor units or screens for displaying images and peripherals responsible for collecting data relating the actions performed by the user.

The system also includes a deformation simulation module for the simulation of the deformation produced in the organs and the nearby tissues during the IORT treatment, implemented by means of algorithms for instantly calculating the radiation dose applied during IORT treatment, and means for recording all the activities carried out by the user and means for generating a dosimetry report.

This system, however, is limited to simulate and plan a IORT treatment in order to estimate the radiation dose that is needed during treatment itself, based on a dosimetry report relative to the entire duration of treatment.

However, currently practiced IORT still has significant limitations and disadvantages.

A first disadvantage is represented by the inappropriate accuracy of the entire distribution of the dose delivered in real time on the irradiated districts with the risk of affecting the clinical studies aimed at determining the dose-effect relationships.

Moreover, instruments to conform the beam of radiation are not yet commercially available, i.e. tools that enable to obtain variable shape and size beams so as to adapt to the district to be treated, in particular in clinical irregular targets, as, for example, in case of lower limbs sarcomas.

Furthermore, due to the current conformation of the instruments, treating tumor beds with extensions greater then 10-12 cm is not possible.

Another disadvantage is represented by the impossibility of knowing the exact layout of the zone to be treated or the "clinical target" and the radiosensitive structures to be safeguarded during the surgery phase, as a real time images acquisition or "imaging on-line" system is not available.

A further disadvantage is the impossibility of knowing, displaying, and documenting the actual distribution of the delivered dose to the zone to be treated and to the radio-sensitive structures, since is not available a treatment planning program or "treatment planning system" (TPS), based on the images acquisition in surgical phase, in more complex morphological situations and characterized by a wide extension of the zone to be treated, such as cancers of the head and neck.

A final disadvantage is the inability to customize the IORT treatment, immediately before the release of the dose, depending on the actual geometry of the anatomical reference, considerably changed after surgery, because of the removal of the tumor mass.

In light of the above, it is, therefore, object of the present invention to provide a radiotherapy system provided with a real time calculating program of the intensity of the electron beam that can be sent to a patient in the zone subjected to surgical removal, contextually the surgical intervention that takes into account the exact calculation of the intensity of the electron beam already sent and the conformation of the region to be treated, during and after surgical removal.

Another object of the invention is to perform a predictive calculation of the IORT treatment plan, which allows having information about the intensity of the electron beam that can be sent to the zone to be treated and information regarding healthy organs for the purpose of optimizing the treatment.

Another object of the invention is to provide a treatment planning system TPS, that uses the electron beam intensity value recorded during the first half of delivering for the accurate determination of monitor units, which have a magnitude proportional to the delivered dose.

It is therefore specific object of the present invention a system for radiotherapy provided with a program for the calculation of the intensity of an electrons beam, the system comprising a mobile electrons accelerator, equipped with a conveyor adapted to convey an electrons beam with a presettable intensity on a zone of or internal to a patient, and constituting the target radiotherapy, an images acquisition apparatus, adapted to detect said zone, an integrated control unit, comprising a bidimensional or tridimensional images display and a computer, said computer being connected to said electrons accelerator and to said images acquisition apparatus, and an active sensing device of the radiation dose deposited by said electrons beam, that can be placed between the distal end of said conveyor and said zone, and that can be connected to said integrated control unit, characterized in that said computer is equipped with a program for the calculation of an intensity of said electrons beam by which said zone can be irradiated, comprising the following steps:

(i) setting a first intensity of said electrons beam, according to functioning and geometric characteristic parameters of said electrons accelerator and/or calculated by Monte Carlo method, and according to at least one predefined image of said zone, said intensity being emitted by said electrons accelerator in a first radiation;

(ii) operating said electrons accelerator to emit a first electrons beam in said first radiation, corresponding to a fraction of said first intensity set in said step (i);

(iii) detecting a real intensity of said first electrons beam during said first radiation, by said radiation sensing device placed in correspondence of said zone;

(iv) acquiring at least one image of said zone by said images acquisition apparatus;

(v) calculating an intermediate intensity of said electrons beam, according to said at least one image acquired in said step (iv) and according to said real intensity of said first electrons beam detected in said step (iii); and (vi) comparing said first intensity of said step (i) with said intermediate intensity of said step (v) to calculate a final intensity of said electrons beam, by which said zone can be irradiated in a second radiation following said first radiation.

Further according to the invention, the calculation of said final intensity of said step (vi) is performed by the following equation:

$$f(i, j, k) = g\left(i, j, \frac{\sum_{l=1}^{k} \rho_l \Delta z}{k \Delta z}\right)$$

where f (i, j, k) is the matrix that represents said final intensity of said step (vi) that can be emitted in said second radiation, index k represents the depth of the medium passed through, g(i, j, 1) is the original matrix of the data related to said first intensity set in said step (i), $\rho_l$ is the electronic density of the water and $\Delta_z$ is the voxel dimension of said at least one image acquired in said step (iv) along the axis of said electrons beam and i and j represent the starting point of the path of the radiation on said zone.

Preferably according to the invention, the calculation of said function ƒ(i, j, k) is performed by statistics simulation, for example of Monte Carlo type, carried on reference data collected in a database of distribution of the intensity of an electrons beam in water, according to different reference geometries of said zone and constructive geometries of said mobile electrons accelerator.

Still according to the invention, said portion emitted in said first radiation in said step (ii) corresponds to almost the half of said first intensity of said step (i).

Further according to the invention, said steps from (i) to (iv) can be recursively run in such a way that, at each new recursion, the final intensity calculated in said step (iv) of the previous recursion coincides with a first intensity settable in said step (i) of the following recursion.

Preferably according to the invention, said active radiation sensing device is an active dosimeter, such as MOSFET or diode or diamond kind, and is equipped with a radiopaque or hypoechoic repere in order to be visible during said step (iv).

Preferred embodiments are defined in the dependent claims.

The present invention will be now described, for illustrative but not limitative purposes, according to its preferred embodiments, with particular reference to the figures of the enclosed drawings, wherein:

FIG. 5A shows a view from below and FIG. 5B shows a side view;

Figure 1:
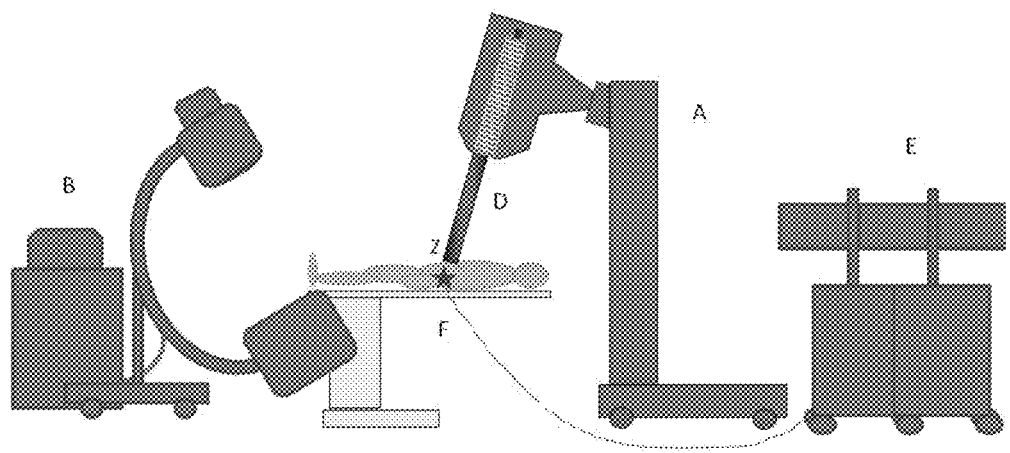
FIG. 1 shows the system object of the invention.
Figure 2:
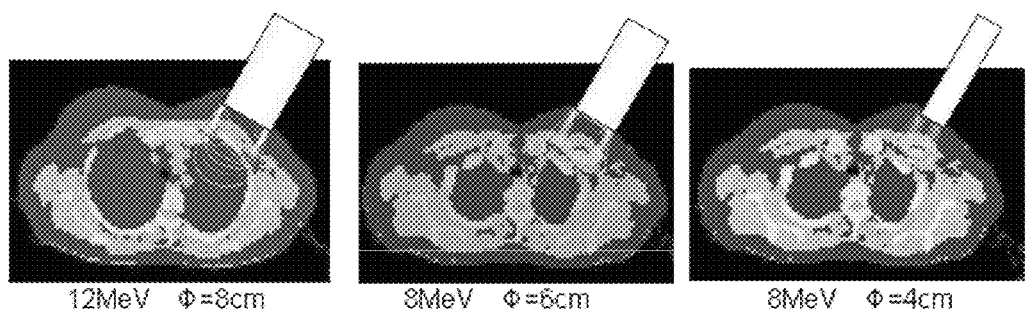
FIG. 2 shows a region, having a particular shape, treated by a conveyor.
Figure 3:
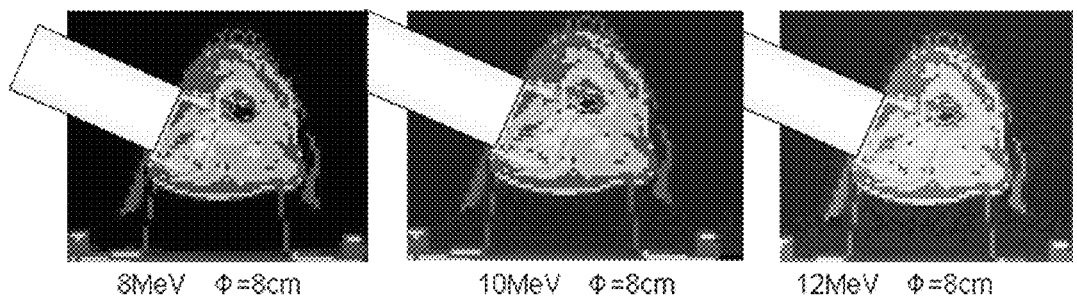
FIG. 3 shows a region having a further particular conformation, treated by a conveyor.
Figure 4:
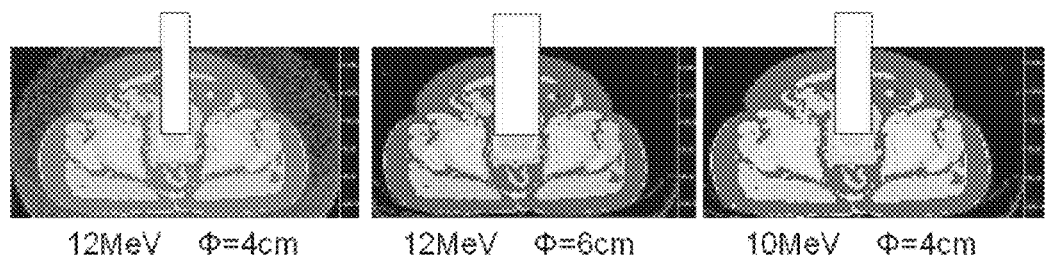
FIG. 4 shows a region, having a further particular conformation, treated by a conveyor.
Figure 5A:
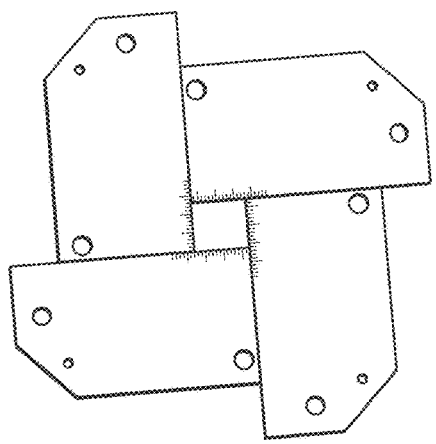
FIGS. 5A and 5B show a prototype of shaper of the beam, where
Figure 5B:
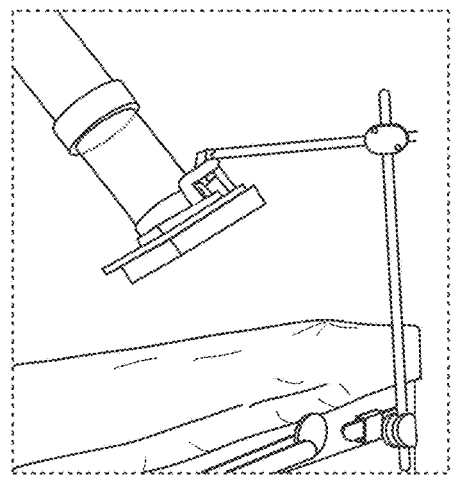

Referring to FIG. 1, the system S includes a dedicated mobile electron accelerator A, an images acquisition apparatus B that allows the acquisition of the intra-operative images during surgery, different from the pre-operative ones, allowing the accurate localization of both the zone Z to be treated of the conveyor D for the delivery of the radiation.

System S also includes an integrated control unit E comprising a 2D and 3D images display and a computer that hosts a treatment planning program or "treatment planning system" (TPS), capable of interfacing with both the images display for image processing necessary for the calculation of the appropriate electron beam intensity and with accelerator A for the management of the specific radiotherapy activity and technical parameters.

System S also comprises a control and verification device F based on an in vivo measurement performed in real time with small size active radiation detectors, such as diodes or MOSFET transistor, which interfaces with the integrated system E.

The TPS program integrated with the accelerator A allows to acquire the images produced by the image display to be used intraoperatively for delineating regions of interest used as a guide during surgical intervention.

System S allows to carry out a real time provisional study of the IORT plan, based on an accurate calculation resulting from processing the images, to calculate the intensity of the electron beam that can be sent to the zone Z to be treated and to the nearby tissues.

TPS is based on the acquisition and elaboration of images, through appropriate computer codes for the co-registration of the images themselves, during pre-operative simulation of the treatment, intra-operative and post-operative.

During the treatment pre-operative simulation, the TPS uses the characteristic dosimetric data of the accelerator A, such as percentage depth dose, called "Percentage Depth Dose" (PDD) and profiles for each energy value and to each type of conveyor D.

The simulation also makes use of conveyors D geometry and the beam modifiers devices that are additional systems to be placed at the end of the conveyor D to shape the field.

TPS algorithms uses Monte Carlo simulations and dosimetric experimental measurements under real conditions.

TPS also includes calculation algorithms for the study of the interaction between the IORT electron beams and tissues of the patient passed through, aimed at calculating the intensity of the electrons beam emitted during intra-operative phase.

TPS program also includes 3D anatomical segmentation models, which allows three dimensions visualization of organs and electronic intensity.

In addition, system S provides data and information exchange between different devices, creating a dedicated unique platform performed using the standard DICOM images and proprietary standards with the accelerator A.

System S has a function which differs according to the different phases in which it operates, in particular:

in the data acquisition preliminary phase, "pre-planning", computed tomography (CT) images are acquired of the anatomical section C subject to surgery using any conventional CT imaging system.

These images are then used for the realization and the optimization of the pre-operative treatment plan, calculating, by module TPS, a first intensity of the electron beam, taking into account the operating and geometric characteristic parameters of the electron accelerator A and/or calculated by the Monte Carlo method, to be delivered through the electron accelerator A in a first irradiation.

During intraoperative phase, the image acquisition apparatus B acquires real-time three-dimensional/volumetric images post surgery that are sent to the TPS with the aim of determining the electron density of the tissues of the zone Z to be treated, in order to differentiate the effectiveness of treatment with respect to tumor tissue and to healthy organs.

These data allow to calculate the distributions of the electron beam intensity also taking into account the presence of beam shapers or surfaces and/or volumes with irregular geometry and therefore to obtain, display and document the intensity distribution of the electron beam released to tissues during the IORT.

Device F detects the real intensity of the first electrons beam in vivo delivered during the IORT treatment.

This measure is compared with the value of the first intensity of the electron beam calculated and set before the treatment, so as then to modify/adapt the dose delivered in real time, avoiding possible undue doses, calculating a final intensity of the beam to be delivered in a second irradiation.

Since the delivery of the IORT treatment is realized in two subsequent parts, a first radiation and a second radiation, according to a broken irradiation path, within the same surgical session, measurements made by the device F in vivo during the first part of delivery are used to optimize the delivery of the electron beam intensity during the second part.

During the post-operative phase, TPS dosimetry calculations are supported by Monte Carlo simulation in order to verify the agreement with the dosimetry calculation of the TPS under realistic conditions, or using images and information acquired during the intra-operative phase.

The electron beam intensity calculation refers to a database of dose distributions in water, calculated by Monte Carlo simulations or experimentally determined, in different reference geometries.

As regards Monte Carlo simulations, the intensity distribution of the electron beam in water and the field magnitudes of the incident beam, derive from the totally detailed description and are characteristic of the IORT mobile linear accelerator used, both in geometry and construction materials terms.

Starting from the distributions of the electron beam intensity in the water, the calculation execution choices are two. A first quick estimate of the electron beam intensity distribution, resulting from the geometry of irradiation choice, is obtained by selecting for each collimator (defined by diameter and cutting angle) and beam energy, the corresponding matrix of the beam intensity of electrons and applying a fast algorithm to compute the equivalent radiological path, such as "ray tracing".

The data obtained through CT scans are used to determine the equivalent path in water through the calculation of known integrals for a specific radius through the regular arrangement in the CT space $$I = \int_{radius} f(x(l), y(l), z(l)) dl$$

where I is the equivalent path to be calculated, and $f(x(1), y(1), z(1))$ is the electron density relative to water.

Indicating the voxel function as $f(i, j, k)$, where voxel means a volumetric pixel, i.e. the voxels are considered as the intersection volume of sets of parallel planes and equally spaced, of indexes (i, j, k), and the length contained in that voxel as the l(i, j, k), the integral I above can be discretized according to the formula $$I = \sum_i \sum_j \sum_k l(i,j,k) f(i,j,k)$$

where $\{i, j, k\} \epsilon$ radius.

The direct calculation of this equation requires the use of an algorithm that scales with the number of terms in the sum, which corresponds to the number of voxels in the regular arrangement in CT space.

Figure 6:
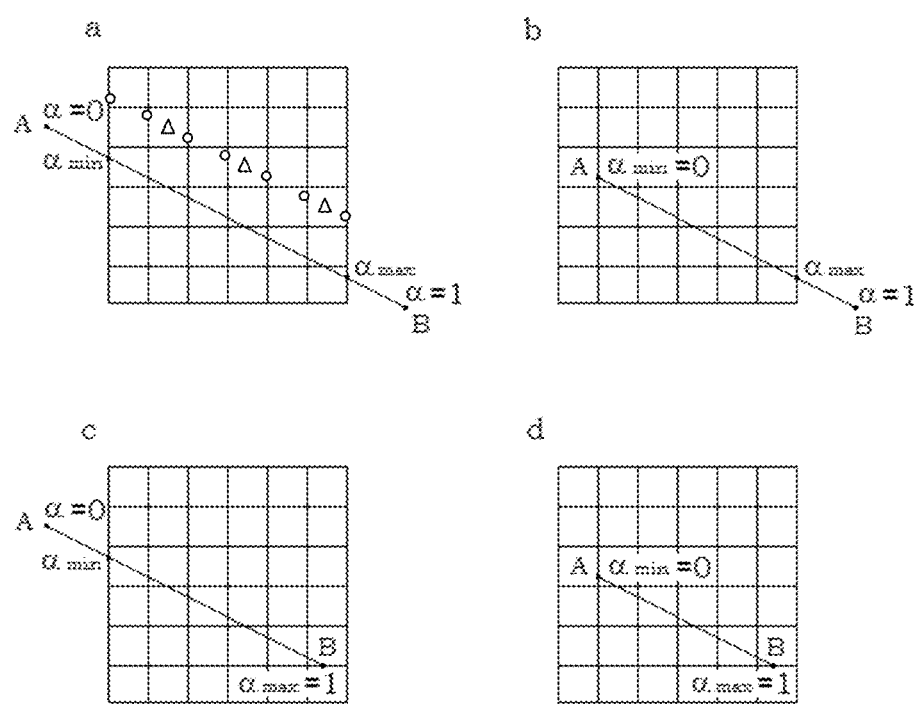
FIGS. 6a-6d show a schematic representation of the algorithm used in the present invention.

Referring to FIG. 6a, the pixels of the CT scan are considered as areas, defined by intersections of orthogonal sets of equally spaced parallel straight lines, in particular two families of parallel straight lines, as shown in FIG.6b.

The intersections of the radius AB are calculated, which represents the radiation, with the equally spaced parallel straight lines.

As the lines are equally spaced, it is needed to determine only the first intersection and generate all the other recursively.

The intersections of the radius AB with the straight lines, are given by the union of two equidistant sets, one set for horizontal straight lines (in solid line) and one for vertical straight lines (dashed).

Referring, for example, to FIG. 6a, the intersections between the radius AB and the straight lines consist of two groups, a first group for the intersections with the horizontal straight lines (triangles) and a second group for the intersections with the vertical straight lines (circles).

The intersections of the radius AB with the pixels are identified by the union of these two groups of intersections.

The identification of this union set is used to determine the X-ray path.

From this identification, the possibility of obtaining the regular arrangement in the CT three-dimensional space follows.

The radius from point A to point B can be represented according to the known formulas:

$$X(\alpha)=X_A+\alpha(X_B-X_A), Y(\alpha)=Y_A+\alpha(Y_B-Y_A), Z(\alpha)=Z_A+\alpha(Z_B-Z_A)$$

where $X_A, Y_A, Z_A$ are the coordinates of point A, and $X_B, Y_B, Z_B$ are the coordinates of point B, $X(\alpha)$, $Y(\alpha)$, $Z(\alpha)$ are the coordinates of the point at issue along the path from A to B.

The parameter $\alpha$, which defines the fraction of the path from A to B, is zero at point A and equal to one at point B.

The intersections of radius AB with the sides of the regular arrangement of the voxels in the CT space are shown in FIGS. 6a through 6d.

Referring to FIG. 6a, if both A and B points fall outside of the regular arrangement in CT space, then the parameter values corresponding to the intersection points of the radius with the edges are given by $\alpha$min and $\alpha$max.

All intersections of the radius AB with single lines must have parametric values that fall in the range between $\alpha$min and $\alpha$max.

Referring to FIG. 6b, the point A is within the regular arrangement in CT space and the value of $\alpha$min is zero.

Referring to FIG. 6c, if point B is within the regular arrangement, then $\alpha$max is equal to one.

Referring to FIG. 6d, in case of both points A and B are within the regular arrangement in CT space, $\alpha$min is equal to zero and $\alpha$max is equal to one.

The solution to the intersection of the radius with the CT voxels derives immediately as it corresponds to the parametric values of the intersections, in the range between $\alpha$min and $\alpha$max of the radius with each orthogonal set of parallel and equally spaced planes.

For each of the coordinate planes, it is obtained a set of values of the parameter $\alpha$ and the three sets of parametric values are neatly combined in a single set; for example, by the combination of the ordered set (1, 4, 7); (2, 5, 8) and (3, 6, 9), the overall set (1, 2, 3, 4, 5, 6, 7, 8, 9) is obtained. The length of the beam contained by a particular voxel, in radius length units is given by the difference between two adjacent parametric values of the overall set.

For each voxel intersection length, the indices of the corresponding voxel are obtained and the products of the length and density are summed over all the intersections for obtaining the radiological path. A more detailed description of the algorithm is given below.

For a regular arrangement in the CT space of (Nx−1, Ny−1, Nz−1) voxel, the set of orthogonal equidistant parallel planes can be described using the following known formulas:

$$X_{plane}(i)=X_{plane}(1)+(i-1)d_x (i=1, \ldots, Nx)$$

$$Y_{plane}(j)=Y_{plane}(1)+(j-1)d_y (j=1, \ldots, Ny)$$

$$Z_{plane}(k)=Z_{plane}(1)+(k-1)d_z (k=1, \ldots, Nz)$$

where dx, dy and dz are the distances between the planes x, y, z respectively.

The quantities dx, dy and dz also correspond to the lengths of the voxel sides.

The parametric values $\alpha$min and $\alpha$max are obtained by the intersection of the radius AB and the sides of the regular arrangement in the CT space.

From the above equations, the parametric values corresponding to the sides are obtained as follows:

if $(XB-XA) \neq 0$ $$\alpha_x(1)=[X_{plane}(1)-X_A]/(X_B-X_A)$$

$$\alpha_x(N_x)=[X_{plane}(N_x)-X_A]/(X_B-X_A)$$

with similar expressions for $\alpha_y(1)$, $\alpha_y(Ny)$, $\alpha_z(1)$, $\alpha_z(Nz)$.

If the denominator (XB−XA) of the equation is zero, then the beam is perpendicular to the x-axis and the corresponding values of $\alpha$ x are undefined.

The same applies to $\alpha$ y and $\alpha$ z.

If the values of $\alpha_x$, $\alpha_y$ or $\alpha_z$ are undefined, then those values are simply dropped in all the following discussion.

In terms of the parametric values given above, the quantities $\alpha$min and $\alpha$max are determined by the following known formulas:

$$\alpha_{min}=\max\{0, \min[\alpha_x(1), \alpha_x(N_x)], \min[\alpha_y(1), \alpha_y(N_y)], \min[\alpha_z(1), \alpha_z(N_z)]\}$$

$$\alpha_{max}=\min\{0, \max[\alpha_x(1), \alpha_x(N_x)], \max[\alpha_y(1), \alpha_y(N_y)], \max[\alpha_z(1), \alpha_z(N_z)]\}$$

where the functions min and max, select from the lists of the corresponding arguments, the terms minimum and maximum, respectively.

If $\alpha$max is less than or equal to $\alpha$min, then the radius does not intersect the regular arrangement in the CT space.

Among all the intersecting planes, there are only a few that have parametric values in the range between $\alpha$min and $\alpha$max.

From the above equations, the range of indices (imin, imax), (jmin, jmax) and (kmin, kmax), corresponding to these particular planes, are given by the following expressions:

for $(XB-XA)>0$ $$i_{min}=N_x-\{X_{plane}(N_x)-[\alpha_{min}(X_B-X_B)]\}/d_x$$

$$i_{max}=1+\lfloor X_I+\alpha_{max}(X_B-X_A)-X_{plane}(1)\rfloor/d_x$$

for $(XB-XA)<0$ $$i_{min}=N_x-\lfloor X_{plane}(N_x)-\alpha_{min}(X_B-X_A)-x_I\rfloor/d_x$$

$$i_{max}=1+\lfloor X_I+\alpha_{min}(X_B-X_A)-X_{plane}(1)\rfloor/d_x$$

with similar expressions for jmin, jmax, kmin, and kmax.

For a given range of indices (imin, imax), (jmin, jmax) and (kmin, kmax), the sets of parametric values $\{\alpha_x\}$, $\{\alpha_y\}$ and $\{\alpha_z\}$, corresponding to the intersections of the radius with the planes are given by the following expression:

for $(XB-XA)>0$ $$\{\alpha_x\}=\{\alpha_x(i_{min}),\ldots,\alpha_x(i_{max})\};$$

per $(XB-XA)<0$ $$\{\alpha_x\}=\{\alpha_x(i_{max}),\ldots,\alpha_x(i_{min})\};$$

where:

$$\alpha_x(i)=\lfloor X_{plane}(i)-X_A\rfloor/(X_B-X_A)=\alpha_x(i-1)+[d_x/(X_B-X_A)]$$

with a similar expression for $\{\alpha_y\}$ and $\{\alpha_x\}$.

The sets $\{\alpha_x\}$, $\{\alpha_y\}$ and $\{\alpha_z\}$ are each ordered in ascending order.

Each term, in each set corresponds to the intersection of the radius with a particular plane. The intersections of the radius with the voxels are obtained grouping the set $\{\alpha_x\}$, $\{\alpha_y\}$ and $\{\alpha_z\}$, in one set.

To include the case in which one or both of the extreme points of the radius can be within the regular arrangement in the CT space, the parametric values of αmin and αmax are added to the unique parametric set.

The terms αmin and αmax and the grouped sets $\{\alpha_x\}$, $\{\alpha_y\}$ and $\{\alpha_z\}$ are expressed by the set $\{\alpha\}$ according to the known formula:

$$\{\alpha\}=\{\alpha_{min},\text{merge}\lfloor\{\alpha_x\},\{\alpha_y\},\{\alpha_z\}\rfloor,\alpha_{max}\}=\{\alpha(0),\ldots,\alpha(n)\}$$

where the last term has an index n given by:

$$n=(i_{min}-i_{min}+1)+(j_{max}-j_{min}+1)+(k_{max}-k_{min}+1)+1$$

two adjacent terms in the set $(\alpha)$ refer to the intersections of the radius with a particular voxel.

For two intersections m and m−1, the length l(m) of the voxel is given by the known expression:

$$l(m)=d_{A,B}[\alpha(m)-\alpha(m-1)]$$

(m=1, ..., n)

in which the quantity $d_{A,B}$ corresponds to the distance of point A from point B, $$d_{A,B}[(X_B-X_A)^2+(Y_B-Y_A)^2+(Z_B-Z_A)^2]^{1/2}$$

The voxel [i(m), j(m), k(m)] which corresponds to the intersections m and m−1 is the one that contains the middle point of the two intersections.

The indices [i(m), j(m), k(m)] are obtained using the following known expressions:

$$i(m)=1+\lfloor X_A+\alpha_{mid}(X_B-X_A)-X_{plane}(1)\rfloor/d_x$$

$$j(m)=1+\lfloor Y_A+\alpha_{mid}(Y_B-Y_A)-Y_{plane}(1)\rfloor/d_y$$

$$k(m)=1+\lfloor Z_A+\alpha_{mid}(Z_B-Z_A)-Z_{plane}(1)\rfloor/d_z$$

where $\alpha_{mid}$ is given by the expression:

$$\alpha_{mid}=[\alpha(m)+\alpha(m-1)]/2$$

The integral I $$I=\int_{radius}f(x(l),y(l),z(l))dl$$

can be now expressed as:

$$I=\sum_{m=1}^{m=n}l(m)f[i(m),j(m),k(m)]=$$

$$d_{A,B}\sum_{m=1}^{m=n}[\alpha(m)-\alpha(m-1)]f[i(m),j(m),k(m)]$$

where n is given by $$n=(i_{max}-i_{min}+1)+(j_{max}-j_{min}+1)+(k_{max}-k_{min}+1)+1$$

l(m) is given by $l(m)=d_{A,B}[\alpha(m)-\alpha(m-1)]$
and the indexes [i(m), j(m), k(m)] can be obtained by $$i(m)=1+\lfloor X_A+\alpha_{mid}(X_B-X_A)-X_{plane}(1)\rfloor/d_x$$

$$j(m)=1+\lfloor Y_A+\alpha_{mid}(Y_B-Y_A)-Y_{plane}(1)\rfloor/d_y$$

$$k(m)=1+\lfloor Z_A+\alpha_{mid}(Z_B-Z_A)-Z_{plane}(1)\rfloor/d_z$$

Figure 7:
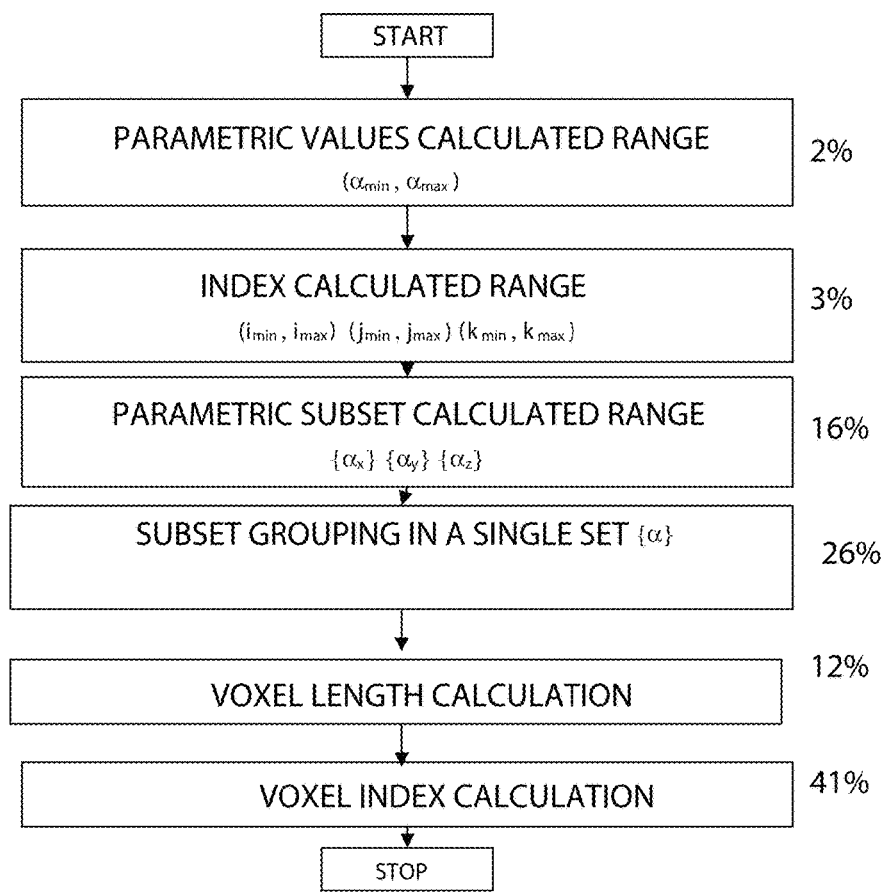
FIG. 7 shows a block diagram of the algorithm.

The algorithm can be modeled in the flow chart of FIG. 7.

For a typical problem, the relative time amount required by the computer processing, for each step of the algorithm, is reported in terms of the respective percentages, on the right of each descriptive block of the step at issue.

This algorithm, applied to a data matrix of electronic densities, obtained from one or more imaging studies of the patient, extracts in each point the equivalent radiological path in water and uses it to sample inputs electron beam intensity matrix.

The result of this sampling operation is then projected voxel by voxel, on a patient radiological image that represent the treatment studied.

The images useful for the determination of the simulation of the dose are obtained in the phase of study/treatment planning, using a pre-surgery morphological image, the during surgery the previous image is suitably deformed and/or co-registered with the one acquired during surgery before IORT treatment.

The calculation can also be carried out directly on the 3D image acquired in the operating room.

A more accurate calculation of the dose is obtained by an analytical formula, by which Monte Carlo data are parameterized, whose parameters were obtained by statistical methods from the dose distribution obtained by Monte Carlo simulation, or alternatively by the experimental measures.

Using this parameterization, the data calculated by Monte Carlo or measured are expressed in an integral analytical representation, applying the analytic fit formula from experimental data or by Monte Carlo.

The percentage depth dose distribution along the central axis of the beam has been represented by means of the known formula:

$$\Gamma_{in}(z) = \frac{(100-p_1)}{1-p_2(z-z_m)} e^{\{-(z-z_m)^2[p_3+p_4(z-z_m)+p_5(z-z_m)^2]\}} + p_1$$

where $z_m$ is the depth of the maximum of the distribution and $p_1, \ldots, p_5$ are the parameters of the fit.

Furthermore, the distribution of percentage depth dose in the outer region to the conveyor is obtained by the original formula:

$$\Gamma_{out} = (100-p_1) \cdot e^{-p_2(Z_{eQ}-Z_{out})^2} + p_1$$

where $p_1$, $p_2$ and $Z_{out}$ are fit parameters.

The dose profile of the "pencil beam" radius is represented by a Gaussian which sigma varies with the depth in water and is separable into two components $\sigma_{tot}^2 = \sigma_G^2 + \sigma_{MCS}^2$, where $\sigma_G$ is the geometric component due to the divergence of the pencil beam at the output of the collimator and $\sigma_{MCS}$ is the component due to multiple Coulomb scattering.

The analytical expression of the geometric component is given by $$\sigma_G = \sigma_1 \left( \sigma_2 z + \frac{SAD}{\sigma_3} \right),$$

while for the component scattering it is $$\sigma_{MCS} = \sigma_4 \left( \frac{Z}{\sigma_5 R_p} \right)^{\sigma_6} \frac{1}{1+e^{\sigma_7(z-\sigma_5 R_p)}}$$

where $\sigma_1, \ldots, \sigma_5$ are the parameters obtained in the fit of the experimental data or by Monte Carlo.

The latter formula is the relevant part of the invention for the dose calculation.

Experimental or generated by the Monte Carlo distributions, when they are managed in the form of "Look Up Tables" or of three-dimensional shape matrices g(i, j, l), are re-sampled to take into account the inhomogeneity encountered by the electrons in their path according to the scheme described below.

Indicating with f(i, j, k) the electron beam intensity matrix and with k the index that identifies the depth in the medium crossed, it is $$f(i, j, k) = g\left(i, j, \frac{\sum_{l=1}^{k} \rho_l \Delta z}{k \Delta z}\right)$$

where g(i, j, l) is the original data matrix, $\rho_l$ is the electron density relative to water and $\Delta_z$ is the size of the voxel along the beam axis, i and j identify the start point of the path of the radiation of said zone (Z).

The information on the density obtained from the pre-surgery images of the patient, is used to modify the parameters of the analytical representation in order to describe more faithfully the effect on the electron beam intensity distribution by different densities encountered by the electron beam.

The dosimetric on-line verification occurs by placing the dosimeter F in one or more points of interest within the surgical incision to be treated.

The active dosimeter F (such as MOSFET, diodes, diamond) is made visible by the intra-operative imaging system (example with a radiopaque marker, hypoechoic, or other) and the reading value is used for comparison with the planned data.

An advantage of the present invention is the possibility to calculate the intensity of the electron beam that can be sent to a zone to be treated to eliminate residual cancer cells, taking into account variations of the morphology of the zone to be treated as a result of surgery and of the radiation already received by the zone to be treated.

A further advantage of the present invention is the possibility to take into account the presence of the beam modifiers dosimetric calculation, taking into account the absorption of the radiation in the same.

The present invention has been described for illustrative but not limitative purposes, according to its preferred embodiments, but it is to be understood that modifications and/or changes can be introduced by those skilled in the art without departing from the relevant scope as defined in the enclosed claims.

The invention claimed is:

1. A system for radiotherapy provided with a program for calculation of intensity of an electron beam, the system comprising
   a mobile electron accelerator, comprising a conveyor adapted to convey an electron beam with a presettable intensity on a zone of or internal to a patient, and forming a target radiotherapy,
   an image acquisition apparatus, configured to detect said zone,
   an integrated control unit, comprising a bidimensional or tridimensional image display and a computer, said computer being connected to said electron accelerator and to said image acquisition apparatus, and
   an active sensing device of a radiation dose deposited by said electron beam, placeable between a distal end of said conveyor and said zone, and connectable with said integrated control unit,
   said computer being provided with a program for calculation of an intensity of said electron beam by which said zone can be irradiated, said program performing the following steps when executed on said computer:
   (i) setting a first intensity of said electron beam, according to functioning and geometric characteristic parameters of said electron accelerator and/or calculated by Monte Carlo method, and according to at least one predefined image of said zone, said intensity being emitted by said electron accelerator in a first radiation;
   (ii) operating said electron accelerator to emit a first electron beam in said first radiation, corresponding to a fraction of said first intensity set in said step (i);
   (iii) detecting a real intensity of said first electron beam during said first radiation, by said active sensing device placed in correspondence of said zone;
   (iv) acquiring at least one image of said zone (Z) by said image acquisition apparatus;
   (v) calculating an intermediate intensity of said electron beam, according to said at least one image acquired in said step (iv) and according to said real intensity of said first electron beam detected in said step (iii); and
   (vi) comparing said first intensity of said step (i) with said intermediate intensity of said step (v) to calculate a final intensity of said electron beam, with which said zone can be irradiated in a second radiation following said first radiation, wherein calculation of said final intensity in said step (vi) is performed by equation $$f(i, j, k) = g\left(i, j, \frac{\sum_{l=1}^{k} \rho_l \Delta z}{k \Delta z}\right)$$

where a function $f(i, j,k)$ is a matrix that comprises data related to said final intensity of said step (vi) that can be emitted in said second radiation, index k represents a depth of medium passed through, $g(i,j,l)$ is an original matrix of data related to said first intensity set in said step (i), $\rho_l$ is electronic density of water and $\Delta_z$ is a voxel dimension of said at least one image acquired in said step (iv) along an axis of said electron beam, wherein i and j represent a starting point of a radiation path on said zone (Z).

2. The system according to claim 1, wherein the calculation of said function $f(i, j,k)$ is performed by statistics simulation carried on reference data collected in a database of distribution of intensity of an electron beam in water, according to different reference geometries of said zone and constructive geometries of said mobile electron accelerator.

3. The system according to claim 2, wherein said statistics simulation is performed in accordance with a Monte Carlo method.

4. The system according to claim 1, wherein said fraction emitted in said first radiation in said step (ii) corresponds to almost half of said first intensity of said step (i), to provide data for the steps from (iv) to (vi).

5. The system according to claim 1, wherein said steps from (i) to (iv) are recursively run in such a way that, at each new recursion, the final intensity calculated in said step (iv) of the previous recursion coincides with a first intensity settable in said step (i) of the following recursion.

6. The system according to claim 1, wherein said active sensing device is an active dosimeter and comprises a radiopaque or hypoechoic repere in order to be visible during said step (iv).

7. The system according to claim 6, wherein said active dosimeter comprises a component selected from MOSFET, diode and diamond.

* * * * *